(12) United States Patent
Chewter et al.

(10) Patent No.: US 8,742,188 B2
(45) Date of Patent: *Jun. 3, 2014

(54) PROCESS FOR PREPARING ETHYLENE AND/OR PROPYLENE AND AN ISO-OLEFIN-DEPLETED OLEFINIC PRODUCT

(75) Inventors: Leslie Andrew Chewter, Amsterdam (NL); Rajaram Ramesh, Amsterdam (NL); Sivakumar Sadasivan Vijayakumari, Amsterdam (NL); Jeroen Van Westrenen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/606,269

(22) Filed: Sep. 7, 2012

(65) Prior Publication Data

US 2013/0245292 A1     Sep. 19, 2013

(30) Foreign Application Priority Data

Sep. 7, 2011   (EP) .................................. 11180326

(51) Int. Cl.
*C07C 2/00*   (2006.01)

(52) U.S. Cl.
USPC ............ 585/326; 549/523; 585/324; 585/640

(58) Field of Classification Search
USPC ........... 549/513, 523; 585/324, 326, 639, 640
See application file for complete search history.

(56) References Cited

U.S. PATENT DOCUMENTS

| | | | |
|---|---|---|---|
| 4,504,688 A | 3/1985 | Herwig et al. | |
| 4,567,029 A | 1/1986 | Wilson et al. | |
| 4,783,555 A * | 11/1988 | Atkins | 568/695 |
| 4,814,519 A * | 3/1989 | Harandi et al. | 568/697 |
| 5,898,091 A * | 4/1999 | Chodorge et al. | 585/647 |
| 6,159,433 A | 12/2000 | Chodorge et al. | |
| 6,235,954 B1 * | 5/2001 | Wu et al. | 585/260 |
| 6,580,009 B2 * | 6/2003 | Schwab et al. | 585/324 |
| 7,402,718 B2 * | 7/2008 | Janssen et al. | 585/638 |
| 8,049,054 B2 * | 11/2011 | Chewter et al. | 585/643 |
| 8,269,056 B2 * | 9/2012 | Van Westrenen et al. | 585/639 |
| 2007/0155999 A1 | 7/2007 | Pujado et al. | |
| 2007/0203380 A1 | 8/2007 | Vora et al. | |

FOREIGN PATENT DOCUMENTS

| | | |
|---|---|---|
| JP | 2009161444 | 7/2009 |
| WO | 2006020083 | 2/2006 |
| WO | WO2007135045 | 11/2007 |

* cited by examiner

*Primary Examiner* — Golam M M Shameem

(57) ABSTRACT

The present invention provides a process for preparing ethylene and/or propylene and an iso-olefin-depleted olefinic product, comprising the steps of:

a) providing a C5 hydrocarbon-comprising stream, comprising C5 cyclopentene and C5 iso-olefins;

b) subjecting the C5 hydrocarbon-comprising stream to an etherification process with methanol and/or ethanol wherein at least part of the C5 iso-olefins are converted with methanol and/or ethanol to an tert-alkyl ether, and retrieving an etherification product stream;

c) separating at least part of the etherification product stream into at least an ether-enriched stream and a first iso-olefin-depleted olefinic product;

d) converting at least part of the tert-alkyl ether in the ether-enriched stream to ethylene and/or propylene by contacting at least part of the ether-enriched stream with a molecular sieve-comprising catalyst at a temperature in the range of from 350 to 1000° C. and retrieving a second olefinic product comprising ethylene and/or propylene.

16 Claims, 1 Drawing Sheet

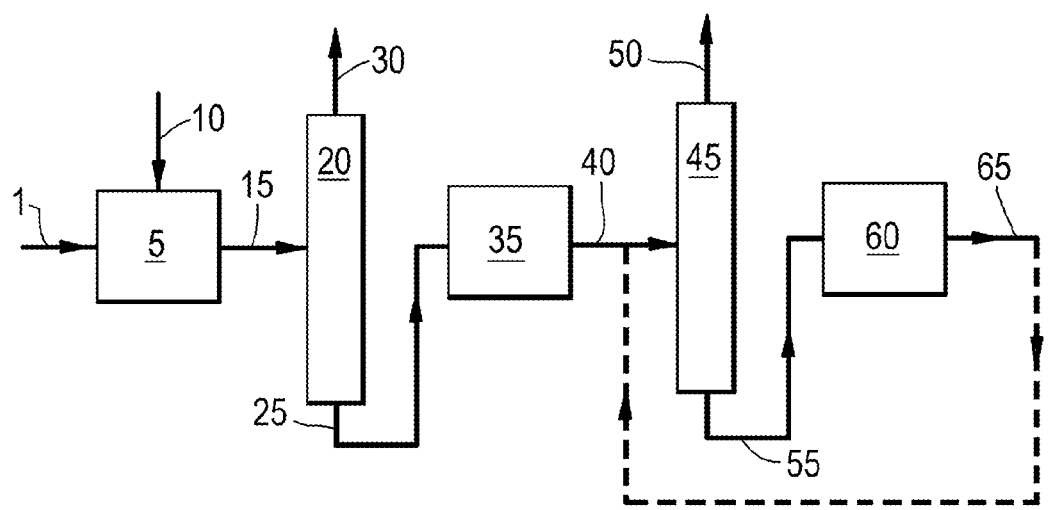

ered, the process of the present invention for preparing ethylene and/or propylene and an iso-olefin-depleted olefinic product, comprises the steps of:

PROCESS FOR PREPARING ETHYLENE AND/OR PROPYLENE AND AN ISO-OLEFIN-DEPLETED OLEFINIC PRODUCT

This application claims the benefit of European Application No. 11180326.8 filed Sep. 7, 2011, which is incorporated herein by reference.

FIELD OF THE INVENTION

The invention relates to a process for preparing ethylene and/or propylene and an iso-olefin-depleted olefinic product.

BACKGROUND TO THE INVENTION

Methanol-to-olefin processes are well described in the art. Typically, methanol-to-olefin processes are used to produce predominantly ethylene and propylene. An example of such a methanol-to-olefin process is described in WO-A 2006/020083. In the process of WO-A 2006/020083, the methanol is first converted into dimethylether (DME) prior to be subjected to a conversion to olefins, thereby reducing the amount of water produced during the conversion to olefins. Both methanol and DME are suitable feedstocks for a Methanol-to-olefin process and therefore such processes are also generally referred to as oxygenate-to-olefin (OTO) processes.

In EP2024303A1, another OTO process is described wherein in addition to oxygenates, also C5 olefins are provided to the OTO process. These C5 olefins are provided as an olefinic co-feed together with the oxygenates. By providing a C5 olefinic co-feed to the OTO process more ethylene and propylene may be produced. According to EP2024303A1, suitable sources for these C5 olefins are for instance C5 hydrocarbon fractions obtained from refinery units such as thermal cracking units, catalytic cracking units, steam cracking units, naphtha (steam) cracking units, gasoil (steam) cracking, hydrowax (steam) cracking, isoprene extraction units, semi-hydrogenation units for removal of C5 diolefins, and Fischer-Tropps synthesis units.

However, these C5 hydrocarbon fractions, in particular those obtained from the effluent of a steam cracking units, contain significant amounts of cyclopentene, especially after semi-hydrogenation units. A disadvantage of providing cyclopentenes to an OTO process is that these cyclopentenes react with methanol to form undesired C6 and C7 naphtpenics through an alkylation reaction of the cyclopentene with methanol without producing ethylene and/or propylene.

A further disadvantage of providing cyclopentenes to an OTO process is that these nathphenic C5 hydrocarbons are relatively high boiling and as such are a major blending component in the fuel pool.

By providing the cyclopentene to an OTO process, less C5 hydrocarbons are available for the fuel pool, which may lead to a discrepancy between the fuel demand and supply.

There is a need in the art for a process, which allow the provision of C5 olefins from a C5 hydrocarbon fraction obtained from for instance steam cracking units, while the cyclopentenes remain available for the transportation fuel pool.

SUMMARY OF THE INVENTION

There is a need in the art for a process, which would allow the provision of C5 olefins from the C5 hydrocarbon fractions obtained from refinery units to an OTO process, while maintaining a continuous supply of C5 hydrocarbons, in particular naphthenic C5 hydrocarbons such as cyclopentenes, to the fuel pool.

It has now been found that it is possible to provide C5 olefins from the C5 hydrocarbon fractions obtained from refinery units, such as steam cracking units, to an OTO process and at the same time maintaining a supply of the naphthenic C5 hydrocarbons to the fuel pool, by reacting iso-olefins in C5 hydrocarbon fraction with an alcohol into a tert-alkyl ether. The iso-olefins are provided to an OTO process as tert-alkyl ethers, while the iso-olefin-depleted C5 hydrocarbon fraction may be used for further purposes.

Accordingly, the present invention provides a process for preparing ethylene and/or propylene and an iso-olefin-depleted olefinic product, comprising the steps of:

a) providing a C5 hydrocarbon-comprising stream, comprising C5 cyclopentene and C5 iso-olefins;

b) subjecting the C5 hydrocarbon-comprising stream to an etherification process with methanol and/or ethanol wherein at least part of the C5 iso-olefins are converted with methanol and/or ethanol to an tert-alkyl ether, and retrieving an etherification product stream;

c) separating at least part of the etherification product stream into at least an ether-enriched stream and a first iso-olefin-depleted olefinic product;

d) converting at least part of the tert-alkyl ether in the ether-enriched stream to ethylene and/or propylene by contacting at least part of the ether-enriched stream with a molecular sieve-comprising catalyst at a temperature in the range of from 350 to 1000° C. and retrieving a second olefinic product comprising ethylene and/or propylene.

By extracting iso-olefins from the C5 hydrocarbon-comprising stream as tert-alkyl ethers and providing the tert-alkyl ethers as a feed to an oxygenate-to-olefins process, ethylene and/or propylene may be produced. At the same time, the remaining C5 hydrocarbon-comprising stream, i.e. iso-olefin-depleted olefinic product, comprising the naphthenic hydrocarbons, in particular cyclopentene, may be provided to the fuel pool or be used as a feedstock for further processes such as alkylation.

A further advantage of the process according to the present invention is that by removing the relatively low boiling iso-olefins from a C5 cut intended to be blended into the fuel pool, the Reid vapor pressure (RVP) of the C5 cut is lowered. As a result, fuel pool RVP increases caused by the addition of low boiling components such as bio-ethanol can be compensated.

An additional advantage of the process according to the invention is that by the extraction of the iso-olefins from the C5 hydrocarbon fraction, there is no need to transport the unreactive hydrocarbons in the C5 hydrocarbon fraction to the OTO unit and subsequently separate them from the OTO reaction effluent and transport them further to the fuel pool.

BRIEF DESCRIPTION OF THE DRAWINGS

In FIG. 1 a schematic representation is given of an embodiment of the process according to the invention.

DETAILED DESCRIPTION OF THE INVENTION

C5 olefins may suitably be used as part of the feed to an OTO process to produce ethylene and/or propylene. In the process according to the present invention a C5 hydrocarbon-comprising stream, comprising C5 cyclic olefins and C5 iso-olefins is provided and part of the olefins in a C5 hydrocarbon-comprising stream, i.e. the iso-olefins, are extracted from the C5 hydrocarbon-comprising stream.

The iso-olefins are extracted by reacting the iso-olefins with an alcohol, in particular methanol and/or ethanol to form tert-alkyl ethers, such as for example tert-amyl methyl ether (TAME) or tert-amyl ethyl ether (TAEE). The formed ethers can be separated from the remainder of the C5 hydrocarbon-comprising stream.

Only iso-olefins, wherein the double bound is located directly adjacent to a tertiary carbon atom can react with methanol to form tert-alkyl ethers. Such iso-olefins are herein referred to as tertiary iso-olefins. Examples of such tertiary iso-olefins include isobutene, 2-methyl-1-butene and 2-methyl-2-butene. An example of an iso-olefin that is not a tertiary iso-olefin is 3-methyl-1-butene. Therefore, in the process according to the present invention at least part of the iso-olefins in the C5 hydrocarbon-comprising fraction should be tertiary iso-olefins.

The tert-alkyl ethers, obtained by extracting the iso-olefins from the C5 hydrocarbon-comprising stream by reacting the iso-olefins with methanol and/or ethanol, are subsequently converted to at least further ethylene and/or propylene in an OTO process.

The remaining C5 hydrocarbons in the C5 hydrocarbon-comprising stream, i.e. iso-olefin-depleted olefinic product, are predominantly comprised of cyclopentene, normal pentenes, mixed pentanes and cyclopentanes. This is a composition suitable to be used as blending feedstock to the fuel pool or to be used as a feedstock for further processes such as alkylation.

The process according to the invention is now described in more detail herein below.

The process according to the present invention is a process for preparing ethylene and/or propylene and an iso-olefin-depleted olefinic product. In the process according to the invention, a C5 hydrocarbon-comprising stream, comprising cyclopentene and iso-olefins, i.e. 2-methyl-1-butene or 2-methyl-2-butene and optionally 3-methyl-1-butene, is provided. C5 hydrocarbon-comprising stream may also comprise normal C5 olefins, i.e. 1-pentene or 2-pentene. The C5 hydrocarbon-comprising stream may also comprise C5 paraffins, including normal pentane and isopentanes. The C5 paraffins are also referred to as mixed pentanes. Preferably, the C5 hydrocarbon-comprising stream comprises in the range of from 40 to 100 wt %, more preferably 75 to 100 wt %, even more preferably 80 to 100 wt %, of C5 hydrocarbons, based on the total weight of the C5 hydrocarbon-comprising stream. Reference herein to C5 hydrocarbons is to hydrocarbons comprising five carbon atoms. Reference herein to hydrocarbons is to molecules comprising only carbon atoms and hydrogen atoms.

The C5 hydrocarbon-comprising stream may also comprise C4 hydrocarbons. Preferably, the C5 hydrocarbon-comprising stream comprises in the range of from 0 to 60 wt %, more preferably 0 to 25 wt % of C4 hydrocarbons, based on the total weight of the C5 hydrocarbon-comprising stream. Reference herein to C4 hydrocarbons is to hydrocarbons comprising four carbon atoms. Preferably, at least part of the C4 hydrocarbons are olefins, in particular iso-olefins. Iso-olefins are preferred as these olefins can form additional tert-alkyl ethers, such as for example methyl tert-butyl ether (MTBE) or ethyl tert-butyl ether (ETBE).

Preferably, the C5 hydrocarbon-comprising stream comprises predominantly C5 hydrocarbons. In that case most of the tert-alkyl ethers formed are TAME and TAEE. This is advantageous as TAME and TAEE, when converted in an OTO process result in a higher ethylene and/or propylene yield compared to for instance MTBE and ETBE. This is particularly advantageous in case the alcohol used in the etherification process is methanol.

Preferably, the C5 hydrocarbon-comprising stream comprises in the range of from 10 to 100 wt % of olefins based on the weight of the hydrocarbons in the C5 hydrocarbon-comprising stream, preferably of from 30 to 100 wt % of olefins based on the weight of the hydrocarbons in the C5 hydrocarbon-comprising stream. Preferably, the C5 hydrocarbon-comprising stream comprises in the range of from 1 to 60 wt % of iso-olefins based on the weight of the olefins in the C5 hydrocarbon-comprising stream, preferably of from 10 to 50 wt % of iso-olefins based on the weight of the olefins in the C5 hydrocarbon-comprising stream.

Preferably, the C5 hydrocarbon-comprising stream comprises in the range of from 1 to 60 wt % of cyclopentene based on the weight of the olefins in the C5 hydrocarbon-comprising stream, more preferably 5 to 55 wt % of cyclopentene.

The C5 hydrocarbon-comprising stream comprises may also comprise C6+ hydrocarbons, in particular C6 hydrocarbons.

Optionally, the C5 hydrocarbon-comprising stream also contains a diluent. Examples of suitable diluents include, but are not limited to, water or steam, nitrogen, argon and methane.

In step (b) of the process according to the invention the C5 hydrocarbon-comprising stream is subjected to an etherification process. In the etherification process the C5 hydrocarbon-comprising stream is contacted with an alcohol, preferably methanol and/or ethanol, in the presence of a suitable etherification catalyst. When the iso-olefins in the C5 hydrocarbon-comprising stream are contacted with the alcohol in the presence of an etherification catalyst, at least part of the iso-olefins are converted with the alcohol to tert-alkyl ethers. Reference herein in to a tert-alkyl ether is to an ether of an alcohol and an iso-olefin. Preferably, the alcohol is methanol and/or ethanol and the tert-alkyl ethers are tert-amyl methyl ether (TAME) or tert-amyl ethyl ether (TAEE), which are tert-alkyl ethers of respectively methanol and ethanol with 2-methyl-1-butene or 2-methyl-2-butene. Optionally, in the presence of isobutene also methyl tert-butyl ether (MTBE) and ethyl tert-butyl ether (ETBE), which are tert-alkyl ethers of respectively methanol and ethanol with isobutene, may be formed. From the etherification process, an etherification product stream is retrieved. The etherification product stream will comprise the formed tert-alkyl ethers and the remainder of the C5 hydrocarbon-comprising stream, i.e. the unreacted components, including cyclopentenes and optionally, normal pentenes, cyclo-pentadienes, mixed pentanes and cyclo-pentanes. In addition, the etherification product stream may also comprise unreacted alcohol. Typically the etherification reaction is performed in the presence of an excess of alcohol, i.e. above reaction stoichiometry with the iso-olefin.

At least part, and preferably all, of the etherification product stream is separated in step (c) into at least an ether-enriched stream and a first iso-olefin-depleted olefinic product, including cyclopentenes and optionally, normal pentenes, cyclo-pentadienes, mixed pentanes and cyclo-pentanes. The separation of the etherification product stream into an ether-enriched stream and an iso-olefin-depleted olefinic product can be done with normal separation means provided in the art. Due to the relatively high boiling points of alcohol, i.e. methanol and/or ethanol, the bulk of the excess alcohol can be directed toward the ether-enriched stream. Alcohol may form an azeotropic mixture with for instance the normal olefins and cyclopentene in the iso-olefin-depleted olefinic product. The methanol concentration in the azeotropic mixture with C5 normal olefins is approximately 12 wt %, based on weight of the azeotropic mixture. The ethanol concentration in the azeotropic mixture with C5 normal olefins is approximately 8 wt %, based on weight of the azeotropic mixture. The methanol concentration in the azeotropic mixture with cyclopentene olefins is approximately 20 wt %, based on weight of the azeotropic mixture. In the case of etherification with a mixed methanol/ethanol stream to produce TAME and TAEE, there are at least two different azeotropes. The alcohol concentration in the azeotropic mixture may depend on the pressure used.

It may be desired to remove the alcohol prior to providing the iso-olefin-depleted olefinic product as feedstock to another process. The alcohol is for instance an undesired component in a feed stream to an alkylation unit. In addition, the alcohol is a valuable feedstock for producing ethylene and propylene and is therefore preferably captured. The alcohol may be extracted from the iso-olefin-depleted olefinic product by a water extraction. In one embodiment, alcohol is separated from hydrocarbons in an extraction column Alcohol and hydrocarbons are fed to the bottom part of the extractor and water to the top section. The column is typically filled with random packing or sieve trays, which enhance alcohol mass-transfer from the hydrocarbon phase to the water phase. Essentially alcohol-free hydrocarbons may be retrieved above the water feed point, and a water/alcohol mixture is the bottom product. The alcohol may separated from the water by distillation and led back to the etherification process, or the water/alcohol mixture may be contacted with a molecular sieve to produce ethylene and/or propylene, for instance by providing the water/alcohol mixture to an OTO unit.

In case, the iso-olefin-depleted olefinic product is provided to the fuel pool, the alcohol is preferably not removed from the iso-olefin-depleted olefinic product, but provided together with the hydrocarbons to the fuel pool. Methanol and in particular ethanol are preferred fuel blending components, in particular if they originate from renewable recourse. Such methanol and ethanol are also referred to as bio-methanol and bio-ethanol. Therefore, the methanol and/or ethanol used in the process according to the invention are preferably bio-methanol and bio-ethanol. By blending bio-methanol and bio-ethanol into the fuel pool the RVP of the fuel pool is typically increased. However, by extracting the low boiling C5 iso-olefins from the C5 hydrocarbon-comprising stream prior to adding the C5 hydrocarbon-comprising stream to the fuel pool, the RVP increase caused by the addition of bio-methanol and bio-ethanol is at least partly off-set. Therefore, in case in step (b) iso-olefins are converted with methanol to TAME, the first iso-olefin-depleted olefinic product preferably comprises the azeotropic mixture of methanol with C5 olefins, more preferably comprises at least 8 wt % methanol, even more preferably 12 wt % methanol, based on the weight of the C5 olefins in the first iso-olefin-depleted olefinic product. Even more preferably, in step (b) iso-olefins are converted with ethanol to TAEE and the first iso-olefin-depleted olefinic product comprises the azeotropic mixture of ethanol with C5 olefins, more preferably comprises at least 4 wt % ethanol, even more preferably 8 wt % ethanol, based on the weight of the C5 olefins in the first iso-olefin-depleted olefinic product.

The iso-olefin-depleted olefinic product may be exported from the process for use as described hereinabove. Preferably, at least part of the first iso-olefin-depleted olefinic product is used as a feed to an alkylation process to produce alkylate. Alternatively, at least part of the first iso-olefin-depleted olefinic product is used as blending components to the fuel pool.

If desired, the iso-olefin-depleted olefinic product may be provided to step (d) of the process as a co-feed. This may be of interest in case of a temporary decreased external C5 demand.

In the process according to the present invention, ethylene and/or propylene are produced in step (d) by converting at least part of the tert-alkyl ethers in the ether-enriched stream to ethylene and/or propylene. At least part of the tert-alkyl ethers in the ether-enriched stream are converted by providing at least part of the ether-enriched stream to a reactor and contacting at least part of the ether-enriched stream with a molecular sieve-comprising catalyst to obtain a second olefinic product, comprising ethylene and/or propylene. Preferably, the olefinic product comprises advantageously at least 50 mol %, in particular at least 50 wt %, ethylene and propylene, based on total hydrocarbon content in the olefinic product. In addition, the second olefinic product may also comprise C4 and C5 olefins as part of a C4-C5 hydrocarbon fraction in the second olefinic product. The ether-enriched stream is contacted with the molecular sieve-comprising catalyst at a temperature in the range of from 350 to 1000° C., preferably of from 350 to 750° C. When the tert-alkyl ethers, and in particular MTBE and/or ETBE, are contacted with molecular sieves, i.e. the molecular sieve in the molecular sieve-comprising catalyst, the tert-alkyl ethers are at least partially converted to at least ethylene and/or propylene, preferably ethylene and propylene. In addition to ethylene and/or propylene, also C4 and C5 olefins may be formed. As the tert-alkyl ethers are oxygenates, the conversion of the tert-alkyl ethers in the ether-enriched stream may be considered as an OTO process and operated as such an OTO process. Process conditions for operating an OTO process are provided herein below.

In a preferred embodiment of step (d), step (d) comprises contacting an oxygenate-comprising feedstock with the molecular sieve-catalyst, wherein the oxygenate-comprising feedstock comprises tert-alkyl ether obtained in step (b) and one or more other oxygenates, preferably at least one of methanol and dimethylether, more preferably methanol. Methanol is preferred in particular when the alcohol used to form the ether is also methanol. The methanol is converted to ethylene and propylene. By using a feedstock that comprises next to the tert-alkyl ether also additional methanol, the ratio of propylene to ethylene in the second olefinic product can be advantageously be increased when using a zeolite comprising catalyst.

The conversion of oxygenates such as methanol and DME, under such conditions, to olefins in the presence of molecular sieve-comprising catalysts is well known in the art. With respect to the tert-alkyl ethers it is believed, without wishing to be bound to a particular theory, that upon contacting the molecular sieve-catalyst, the tert-alkyl ether decomposes into its corresponding alcohol, i.e. methanol and/or ethanol, and iso-olefin, i.e. isopentene and optionally isobutene. This decomposition reaction is acid-catalysed. Therefore, preferably the molecular sieve-comprising catalyst comprises acid groups. Some molecular sieves are acidic by nature, whereas other molecular sieve-comprising catalysts comprise binder, support, matrix or other materials comprising acid groups. Even theoretically non-acidic molecular sieves typically comprise some residual acid groups introduced during preparation of the molecular sieve and/or molecular sieve-comprising catalyst. In the absence of any acid groups in the molecular sieve-comprising catalyst it may be preferred to add such groups either by treating the molecular sieve-comprising catalyst to introduce such groups essentially at the surface of the catalyst through impregnation with an acid that resides on the catalyst after calcination, for instance by treating the molecular sieve-comprising catalyst with an acid, such as phosphoric acid, or adding an acid component to catalyst formulation comprising the molecular sieve-comprising catalyst, such as alumina.

Alternatively, the oxygenate-comprising feedstock is contacted with an acid catalyst, prior to contacting the molecular sieve-comprising catalyst. This may for instance be done by passing oxygenate-comprising feedstock through an acid catalyst comprising bed or by passing the feedstock through an acid grid or filter. Preferably, the oxygenate-comprising feedstock is contacted with the acid catalyst at a temperature above 150° C. More preferably, the oxygenate-comprising feedstock is contacted with the acid catalyst at a temperature above 350° C.

Preferably, steam is present as the tert-alkyl ether contacts the catalyst. Steam is believed to increase the selectivity of the reaction.

At least part of the alcohol, preferably methanol and/or ethanol, obtained following the decomposition of the tert-alkyl ether is subsequently converted to ethylene and/or propylene over the molecular sieve-comprising catalyst under the process conditions applied. Any residual methanol in the ether-enriched stream is also converted under these conditions.

As mentioned hereinabove it is believed that upon contact with the molecular sieve-comprising catalyst, the tert-alkyl ether decomposes into an alcohol and an iso-olefin, for instance isopentene. Depending on the nature of the molecular sieve in the molecular sieve-comprising catalyst, the obtained iso-olefins are either, at least partially, converted to ethylene and/or propylene or remain unconverted.

Any unconverted iso-olefins are retrieved from the process as part of the second olefinic product. In addition to any unconverted iso-olefins, the second olefinic product may also comprises C4 and C5 olefins as part of a C4+ hydrocarbon fraction, preferably C4-C5 hydrocarbon fraction, produced as by-product in the conversion of oxygenates to ethylene and/or propylene. Preferably, the C5, and optionally C4, olefins in the second olefinic product are at least partially converted by contacting, at least part of, the C5 olefins with a zeolite-comprising catalyst in a further step (e). This can be done by recycling part of C5 olefins in the C4+ hydrocarbon fraction in the second olefinic product to be contacted again with the catalyst in step (d), i.e. in case the molecular sieve-comprising catalyst of step (d) is a zeolite-comprising catalyst. Alternatively, the C5 olefins in the second olefinic product may be converted in a separate unit, reactor or reactor zone downstream of the OTO reactor.

This is particularly preferred where molecular sieve-comprising catalyst in step (d) comprises at least one SAPO, AlPO, or MeAlPO type molecular sieve, preferably SAPO-34. These catalysts are less suitable for converting iso-olefins. Preferably, the C4 olefins are contacted with the zeolite-comprising catalyst at a reaction temperature of 350 to 1000° C., preferably from 350 to 750° C., more preferably 450 to 700° C., even more preferably 500 to 650° C.; and a pressure from 0.1 kPa (1 mbar) to 5 MPa (50 bar), preferably from 100 kPa (1 bar) to 1.5 MPa (15 bar). Optionally, the stream comprising C4 olefins also contains a diluent. Examples of suitable diluents include, but are not limited to, water or steam, nitrogen, argon, paraffins and methane. Under these conditions, at least part of the C5 olefins are converted to a further olefinic product, comprising ethylene and/or propylene. The further olefinic product may be combined with the olefinic product obtained in step (d). Such a separate process step directed at converting C5 olefins to ethylene and propylene is also referred to as an olefin cracking process (OCP).

In the process according to the invention, the C5 hydrocarbon-comprising stream may be any C5 hydrocarbon-comprising stream. The C5 hydrocarbon-comprising stream is typically an external stream. Examples of such streams are the C5 or C4-C5 fractions of the effluent of a refinery unit such as thermal cracking units, catalytic cracking units, steam cracking units, naphtha (steam) cracking units, gasoil (steam) cracking units, hydrowax (steam) cracking units, Fischer-Tropps hydrocarbon effluent. A particularly preferred C5 hydrocarbon-comprising stream is the C5 cut of an FCC effluent or naphtha (steam) cracker, pentadiene extraction units and semi-hydrogenation units for removal of C5 diolefins.

In the process according to the invention, iso-olefins are reacted with methanol and/or ethanol in an etherification process. The etherification process may be any suitable etherification process available in the art for etherifying methanol, ethanol and iso-olefins to tert-alkyl ethers. Reference is made to the Handbook of MTBE and Other Gasoline Oxygenates, H. Hamid and M. A. Ali ed., $1^{st}$ edition, Marcel Dekker, New York, 2004, pages 65 to 223, where several established process and catalyst for preparing tert-alkyl ethers such as TAME, TAEE, but also MTBE and ETBE are described. In particular reference is made to chapter 9, pages 203 to 220 of the Handbook of MTBE and Other Gasoline Oxygenates, wherein suitable commercial etherification processes are described. A preferred etherification process is an etherification process wherein the iso-olefins are converted with methanol to a tert-alkyl ether in the presence of a catalyst. Any homogeneous or heterogeneous Brönsted acid may be used to catalyze the etherification reaction. Such catalyst include: sulfuric acid, zeolites, pillared silicates, supported fluorocarbonsulphonic acid polymers and protonated cation-exchange resins catalyst, preferred catalyst are protonated cation-exchange resins catalyst due to the higher catalytic activity and the bound acid sites. A commonly used catalyst is Amberlyst 15.

Preferably, the iso-olefins are converted with an alcohol, preferably methanol and/or ethanol, more preferably methanol, to a tert-alkyl ether at a temperature in the range of from 30 to 100° C., more preferably 40 to 80° C. Preferably, the iso-olefins are converted with methanol and/or ethanol to a tert-alkyl ether at a pressures in the range of from 5 to 25 bar, more preferably 6 to 20 bar.

The iso-olefins may be converted with methanol and/or ethanol to a tert-alkyl ether in any etherification process, however, one preferred etherification process is based on a reactive distillation, which allows for a continuous etherification and separation of the formed ethers.

The C5 hydrocarbon-comprising stream can comprise diolefins. Examples of such diolefins include isoprene, piperylene and cyclopentadiene. Preferably, the C5 hydrocarbon-comprising stream comprises in the range of from 0 to 0.5 wt %, preferably 0 to 0.1, more preferably, 0 to 0.01 wt % of diolefins, based on the weight of the hydrocarbons in the hydrocarbon-comprising stream. Most preferably, the hydrocarbon-comprising stream does not contain diolefins. Diolefins may react to from undesired higher hydrocarbon compounds.

Preferably, the part of the C5 hydrocarbon-comprising stream subjected to the etherification process is treated to remove at least part of any diolefins prior to being subjected to the etherification process. C5 diolefins such as isoprene, piperylene and cyclopentadiene are valuable products and may be removed from the C5 hydrocarbon-comprising stream by extraction or distillation. Cyclopentadiene can be dimerised to di-cyclopentadiene. In addition or instead of the above described removal of diolefins from the C5 hydrocarbon-comprising stream, it is preferred that the C5 hydrocarbon-comprising stream is selectively hydrogenated prior to being subjected to the etherification process to remove at least part of any diolefins, by hydrogenating the diolefins to mono-olefins and/or paraffins, preferably to mono-olefins.

In the present invention, in step (d) an oxygenate-comprising feedstock is converted in an oxygenate-to-olefins process, in which an oxygenate feedstock is contacted in an OTO zone with an oxygenate conversion catalyst under oxygenate conversion conditions, to obtain a conversion effluent comprising lower olefins. Reference herein to an oxygenate feedstock is to an oxygenate-comprising feedstock, including any feedstock comprising at least part of the tert-alkyl ether produced in step (b). An example of such an oxygenate-comprising feedstock is a feedstock comprising at least part of the ether-enriched stream obtained in step (c). In the OTO zone, at least part of the feedstock is converted into an olefinic product, i.e. a product containing one or more olefins, including ethylene and/or propylene.

The oxygenate-comprising feedstock comprises at least one tert-alkyl ether, preferably selected from the group of methyl tert-butyl ether (TAME) or ethyl tert-butyl ether (TAEE). Other tert-alkyl ethers may be comprised in the feedstock, such as tert-alkyl ethers obtained by the reaction between an alcohol and isobutene.

Further oxygenates used in step (d) the process according to the invention may preferably be oxygenates, which comprise at least one oxygen-bonded alkyl group. The alkyl group preferably is a C1-C8 alkyl group, more preferably C1-C4 alkyl group, i.e. comprises 1 to 5, respectively, 4 carbon atoms; more preferably the alkyl group comprises 1 or 2 carbon atoms and most preferably one carbon atom. Examples of oxygenates that can be used in the oxygenate-comprising feedstock include alcohols and ethers. Examples of preferred oxygenates include alcohols, such as methanol, ethanol, propanol; and dialkyl ethers, such as dimethylether, diethylether, methylethylether. Preferably, the further oxygenate is methanol or dimethylether, or a mixture thereof.

Preferably the oxygenate-comprising feedstock comprises at least 50 wt % of oxygenate, based on the total of hydrocarbons and oxygenates in the oxygenate-comprising feedstock, more preferably at least 70 wt %. Reference herein to hydrocarbons is to molecules comprising at least carbon atoms and hydrogen atoms.

The oxygenate feedstock can comprise an amount of diluents. During the conversion of the oxygenates, steam is produced as a by-product, which serves as an in-situ produced diluent. Optionally additional steam is added as diluent. The amount of additional diluent that needs to be added depends on the in-situ water make, which in turn depends on the composition of the oxygenate-comprising feed. Where methanol produces 1 mol of water per mol of carbon atoms supplied to the process, TAME, for example only produces 0.17 mol of water per 1 mol of carbon atoms supplied to the process. Where the diluent is water or steam, the molar ratio of oxygenate to diluent is between 10:1 and 1:20. In case, the oxygenate-comprising feedstock comprises in the range of from 0.01 to 50 wt %, preferably of from 1 to 10 wt %, of tert-alkyl ether, based on the oxygenates in the oxygenate-comprising feedstock, the molar ratio of oxygenate to diluent is preferably in the range of from 3:1 to 1:5, preferably 2:1 to 1:2. In case, the oxygenate-comprising feedstock comprises in the range of from 50 to 100 wt %, preferably 60 to 95 wt %, of tert-alkyl ether, based on the oxygenates in the oxygenate-comprising feedstock, the molar ratio of oxygenate to diluent is preferably in the range of from 1:3 to 1:15, preferably 1:4 to 1:10.

Due to the low in-situ water make of tert-alkyl ethers, the use of diluents other than water may be preferred, in particular when the catalyst is sensitive to hydrothermal deactivation. Other suitable diluents include inert gases such as nitrogen, but may also include paraffins.

Preferably, in addition to the oxygenate, an olefinic co-feed is provided along with and/or as part of the oxygenate feedstock. Reference herein to an olefinic co-feed is to an olefin-comprising co-feed. The olefinic co-feed preferably comprises C4 and higher olefins, more preferably C4 and C5 olefins. Preferably, the olefinic co-feed comprises at least 25 wt %, more preferably at least 50 wt %, of C4 olefins, and at least a total of 70 wt % of C4 hydrocarbons, based on weight of the olefinic co-feed.

Preferably, at least 70 wt % of the olefinic co-feed, during normal operation, is formed by a recycle stream of a C4+ hydrocarbon fraction from the OTO conversion effluent, preferably at least 90 wt % of olefinic co-feed, based on the whole olefinic co-feed, is formed by such recycle stream. In order to maximize production of ethylene and propylene, it is desirable to maximize the recycle of C4 olefins in the effluent of the OTO process. As described herein above, this can be done by recycling at least part of the C4+ hydrocarbon fraction, preferably a C4-C5 hydrocarbon fraction, more preferably C4 hydrocarbon fraction, in the olefinic product, which is retrieved as the OTO effluent. However, a certain part thereof, such as between 1 and 5 wt %, needs to be withdrawn as purge, since otherwise saturated hydrocarbons, in particular C4 saturated hydrocarbons (butane) would build up in the process, which are substantially not converted under the OTO reaction conditions.

The preferred molar ratio of oxygenate in the oxygenate feedstock to olefin in the olefinic co-feed provided to the OTO conversion zone depends on the specific oxygenate used and the number of reactive oxygen-bonded alkyl groups therein. Preferably, the molar ratio of oxygenate to olefin in the total feed, oxygenate feed and olefinic co-feed, lies in the range of 20:1 to 1:10, more preferably in the range of 18:1 to 1:5, still more preferably in the range of 15:1 to 1:3, even still more preferably in the range of 12:1 to 1:3.

A further advantage of using the selected tert-alkyl ethers as part of the oxygenate-comprising feedstock is that these ethers provide both an oxygenate, being methanol or ethanol, and an olefin, being at least isopentene, to the process in the form of a single molecule, which decomposes when contacted with the catalyst. This has the advantage that both reactants, i.e. an oxygenate and an olefin, may be provided in a single feed component. For purposes of calculating the molar ratio of oxygenate to olefin in the total feed, the olefins provided to the process as part of the tert-alkyl ether must also be taken into account.

Using the selected tert-alkyl ethers as part of the oxygenate-comprising feedstock allows for instance a more convenient transport of the feedstock, storage of the feedstock and pretreatment of the feedstock. Furthermore, the handling and storage of tert-alkyl ether liquids is less complicated, providing further advantages.

A variety of OTO processes is known for converting oxygenates to an olefin-containing product, as already referred to above. One such process is described in WO-A 2006/020083. Processes integrating the production of oxygenates from synthesis gas and their conversion to light olefins are described in US20070203380A1 and US20070155999A1.

Catalysts suitable for converting the oxygenate-comprising feedstock preferably include molecular sieve-comprising catalyst compositions. Such molecular sieve-comprising catalyst compositions typically also include binder materials, matrix material and optionally fillers. Suitable matrix materials include clays, such as kaolin. Suitable binder materials include silica, alumina, silica-alumina, titania and zirconia, wherein silica is preferred due to its low acidity.

Molecular sieves preferably have a molecular framework of one, preferably two or more corner-sharing $[TO_4]$ tetrahedral units, more preferably, two or more $[SiO_4]$, $[AlO_4]$ and/or $[PO_4]$ tetrahedral units. These silicon, aluminum and/or phosphorous based molecular sieves and metal containing silicon, aluminum and/or phosphorous based molecular sieves have been described in detail in numerous publications including for example, U.S. Pat. No. 4,567,029. In a preferred embodiment, the molecular sieves have 8-, 10- or 12-ring structures and an average pore size in the range of from about 3 Å to 15 Å.

Suitable molecular sieves are silicoaluminophosphates (SAPO), such as SAPO-17, -18, -34, -35, -44, but also SAPO-5, -8, -11, -20, -31, -36, -37, -40, -41, -42, -47 and -56; aluminophosphates (AlPO) and metal substituted (silico)aluminophosphates (MeAlPO), wherein the Me in MeAlPO refers to a substituted metal atom, including metal selected from one of Group IA, IIA, IB, IIIB, IVB, VB, VIIB, VIIB, VIIIB and Lanthanide's of the Periodic Table of Elements, preferably Me is selected from one of the group consisting of Co, Cr, Cu, Fe, Ga, Ge, Mg, Mn, Ni, Sn, Ti, Zn and Zr.

Alternatively, the conversion of the oxygenate feedstock may be accomplished by the use of an aluminosilicate-comprising catalyst, in particular a zeolite-comprising catalyst. Suitable catalysts include those containing a zeolite of the ZSM group, in particular of the MFI type, such as ZSM-5, the MTT type, such as ZSM-23, the TON type, such as ZSM-22, the MEL type, such as ZSM-11, the FER type. Other suitable zeolites are for example zeolites of the STF-type, such as SSZ-35, the SFF type, such as SSZ-44 and the EU-2 type, such as ZSM-48.

Aluminosilicate-comprising catalysts, and in particular zeolite-comprising catalysts, have the additional advantage that in addition to the conversion of methanol or ethanol, these catalysts also induce the conversion of olefins to ethylene and/or propylene. As a result, at least part of the olefins obtained as the tert-alkyl ether is decomposed into methanol or ethanol and the corresponding iso-olefin, may also be converted into ethylene and/or propylene. Furthermore, these aluminosilicate-comprising catalysts, and in particular zeolite-comprising catalysts, are particularly suitable for use as the catalyst in an OCP. Particular preferred catalyst for the OCP reaction, i.e. converting part of the olefins in the second olefinic product, are catalysts comprising at least one zeolite selected from MFI, MEL, TON and MTT type zeolites, more preferably at least one of ZSM-5, ZSM-11, ZSM-22 and ZSM-23 zeolites.

In one preferred embodiment, the molecular sieve in the molecular sieve-comprising catalyst of step (d) is a non-zeolitic molecular sieve, while part of the olefinic product retrieved in step (d), in particular at least part of the C4+ fraction containing olefins, is provided to a subsequent separate OCP unit with a zeolite-comprising catalyst and the C4+ hydrocarbon fraction is at least partially converted by contact with the zeolite-comprising catalyst in a step (e).

Preferred catalysts, for both the OTO reaction in step (d) as well as an optional OCP reaction in step (e), comprise a more-dimensional zeolite, in particular of the MFI type, more in particular ZSM-5, or of the MEL type, such as zeolite ZSM-11. Such zeolites are particularly suitable for converting olefins, including iso-olefins, to ethylene and/or propylene. The zeolite having more-dimensional channels has intersecting channels in at least two directions. So, for example, the channel structure is formed of substantially parallel channels in a first direction, and substantially parallel channels in a second direction, wherein channels in the first and second directions intersect. Intersections with a further channel type are also possible. Preferably the channels in at least one of the directions are 10-membered ring channels. A preferred MFI-type zeolite has a Silica-to-Alumina ratio SAR of at least 60, preferably at least 80. The oxygenate conversion catalyst can comprise at least 1 wt %, based on total molecular sieve in the oxygenate conversion catalyst, of the molecular sieve having more-dimensional channels, preferably at least 5 wt %, more preferably at least 8 wt %.

Particular preferred catalysts, for both the OTO reaction in step (d) as well as an optional OCP reaction in step (e), include catalysts comprising one or more zeolite having one-dimensional 10-membered ring channels, i.e. one-dimensional 10-membered ring channels, which are not intersected by other channels. Preferred examples are zeolites of the MTT and/or TON type. Preferably, the catalyst comprises at least 40 wt %, preferably at least 50% wt of such zeolites based on total zeolites in the catalyst.

In a particularly preferred embodiment the catalyst, for both the OTO reaction in step (d) as well as an optional OCP reaction in step (e), comprises in addition to one or more one-dimensional zeolites having 10-membered ring channels, such as of the MTT and/or TON type, a more-dimensional zeolite, in particular of the MFI type, more in particular ZSM-5, or of the MEL type, such as zeolite ZSM-11.

The catalyst, for both the OTO reaction in step (d) as well as an optional OCP reaction in step (e), may comprise phosphorous as such or in a compound, i.e. phosphorous other than any phosphorous included in the framework of the molecular sieve. It is preferred that an MEL or MFI-type zeolites comprising catalyst additionally comprises phosphorous. The phosphorous may be introduced by pre-treating the MEL or MFI-type zeolites prior to formulating the catalyst and/or by post-treating the formulated catalyst comprising the MEL or MFI-type zeolites. Preferably, the catalyst comprising MEL or MFI-type zeolites comprises phosphorous as such or in a compound in an elemental amount of from 0.05 to 10 wt % based on the weight of the formulated catalyst. A particularly preferred catalyst comprises phosphor-treated MEL or MFI-type zeolites having SAR of in the range of from 60 to 150, more preferably of from 80 to 100. An even more particularly preferred catalyst comprises phosphor-treated ZSM-5 having SAR of in the range of from 60 to 150, more preferably of from 80 to 100.

It is preferred that molecular sieves in the hydrogen form are used in the oxygenate conversion catalyst in step (d), e.g., HZSM-22, HZSM-23, and HZSM-48, HZSM-5. Preferably at least 50 wt %, more preferably at least 90 wt %, still more preferably at least 95 wt % and most preferably 100 wt % of the total amount of molecular sieve used is in the hydrogen form. It is well known in the art how to produce such molecular sieves in the hydrogen form.

The reaction conditions of the oxygenate conversion in step (d) include a reaction temperature of 350 to 1000° C., preferably from 350 to 750° C., more preferably 450 to 700° C., even more preferably 500 to 650° C.; and a pressure from 0.1 kPa (1 mbar) to 5 MPa (50 bar), preferably from 100 kPa (1 bar) to 1.5 MPa (15 bar).

Typically the catalyst deactivates in the course of the process, primarily due to deposition of coke on the catalyst.

Conventional catalyst regeneration techniques can be employed to remove the coke. It is not necessary to remove all the coke from the catalyst as it is believed that a small amount of residual coke may enhance the catalyst performance and additionally, it is believed that complete removal of the coke may also lead to degradation of the molecular sieve. This applies to both the catalyst used in step (d) of the process as well as the catalyst in the optional step (e) of the process.

The catalyst particles used in the process of the present invention can have any shape known to the skilled person to be suitable for this purpose, for it can be present in the form of spray dried catalyst particles, spheres, tablets, rings, extrudates, etc. Extruded catalysts can be applied in various shapes, such as, cylinders and trilobes. If desired, spent oxygenate conversion catalyst can be regenerated and recycled to the process of the invention. Spray-dried particles allowing use in a fluidized bed or riser reactor system are preferred. Spherical particles are normally obtained by spray drying. Preferably the average particle size is in the range of 1-200 µm, preferably 50-100 µm.

Both the OTO process of step (d) as the optional OCP process of step (e) may be operated in a fluidized bed or moving bed, e.g. a fast fluidized bed or a riser reactor system, and also in a fixed bed reactor or a tubular reactor. A fluidized bed or moving bed, e.g. a fast fluidized bed or a riser reactor system are preferred.

In step (d) of the process a second olefinic product stream comprising ethylene and/or propylene is retrieved. As described herein above, in step (e) a further olefinic product stream comprising ethylene/and propylene may be obtained. The ethylene and/or propylene may be separated from the remainder of the components in the olefinic products. Preferably the olefinic product and further olefinic product at least partially, and preferably fully, combined prior to separating the ethylene and/or propylene from the remaining components. Where the olefinic product comprises ethylene, least part of the ethylene may be further converted into at least one of polyethylene, mono-ethylene-glycol, ethylbenzene and styrene monomer. Where the olefinic product comprises propylene, at least part of the propylene may be further converted into at least one of polypropylene and propylene oxide.

DETAILED DESCRIPTION OF THE DRAWINGS

In FIG. 1, a process according to the present invention is schematically represented. In FIG. 1, C5 hydrocarbon-comprising stream 1 comprising cyclopentene and C5 iso-olefins is provided to etherification zone 5, together with methanol 10. In etherification zone 5, C5 hydrocarbon-comprising stream 1 is contacted with methanol 10 over an etherification catalyst, such as for instance a protonated cationic-exchange resin. Etherification product 15 is retrieved from etherification zone 5 and provided to separation zone 20, wherein etherification product 15 is separated into an ether-enriched stream 25 and an iso-olefin-depleted olefinic product 30. Optionally, zones 5 and 20 are combined into a reactive distillation zone, wherein iso-olefins are reacted with methanol to tert-alkyl ethers, while continuously separating tert-alkyl ether from the reaction mixture. Optionally, zones 5 and 20 allow for the recycle of part of the iso-olefin depleted stream in case not all of the iso-olefins are converted to tert-alkyl ether in a single pass process.

Iso-olefin-depleted olefinic product 30 is withdrawn from the process and may be provided to the fuel pool. Ether-enriched stream 25 is provided to oxygenate-to-olefin zone 35. In oxygenate-to-olefin zone 35, ether-enriched stream 25 is contacted with a molecular sieve-comprising catalyst, for example a catalyst comprising ZSM-5, such as a catalyst comprising 50 wt % of ZSM-5 and 50 wt % ZSM-23, based on the zeolite content in the catalyst, or a catalyst comprising SAPO-34. Optionally, additional oxygenate, such as methanol or dimethylether, olefins and water are added to oxygenate-to-olefin zone 35 (not shown). Second olefinic product 40, comprising ethylene and/or propylene is retrieved from oxygenate-to-olefin zone 35. Preferably, second olefinic product 40 is further treated to separate the ethylene and/or propylene from the remainder of second olefinic product 40. Therefore, preferably second olefinic product 40 is provided to second separation zone 45. Second separation zone 45 may for instance include a quench tower set for receiving olefinic product 40. In the quench tower high boiling components such as water may be removed, the remaining stream may be compressed in a multi stage compressor zone, with interstage cooling and separation of condensed phases. The compressed vapour stream may be provided to a combination of a de-ethaniser and a de-propaniser to separate the compressed vapour stream into at least ethylene and/or propylene and a C4+ hydrocarbon fraction, comprising C5 and optionally C4 olefins. The ethylene and/or propylene may be retrieved from second separation zone 45 separately or as a mixture via one or more streams 50. C5 olefins may be retrieved as part of stream 55. Stream 55 may also contain higher hydrocarbons, i.e. C6+ olefins and C4+ paraffins, however preferably any C6+ hydrocarbons are separated in second separation section 45 from the C5, and optionally C4, hydrocarbons and retrieved as a separate C6+ hydrocarbon stream (not shown). C5, and optionally C4, olefins in the second olefinic product, and optionally at least a part of the C6+ olefins in the second olefinic product, may be recycled back to OTO zone 35 (not shown). Alternatively, for instance in case a non-zeolite catalyst such as SAPO-34 is used in OTO zone 35, at least part of the C5, and optionally C4, olefins in the second olefinic product, and optionally at least a part of the C6+ olefins in the second olefinic product, are provided to reactor zone 60, which is operated as an Olefin Cracking Process (OCP). In reactor zone 60, stream 55 is contacted with a zeolite comprising catalyst, for example a catalyst comprising ZSM-5, such as a catalyst comprising 50 wt % of ZSM- and 50 wt % ZSM-23, based on the zeolite content in the catalyst. Further olefinic product 65 is retrieved from reactor zone 60. Further olefinic product 65 comprises further ethylene and/or propylene. Optionally, further olefinic product 65 is recycled back (dotted line) to second separation unit 45. In that case, preferably part of further olefinic product 65 is withdrawn from the process as a purge stream to prevent the build-up of paraffinic hydrocarbons in further olefinic product 65 (not shown).

EXAMPLES

The invention is illustrated by the following non-limiting examples.

Example 1

Several molecular sieves were tested to show their ability to convert TAME to an olefinic product. To test the molecular sieves for catalytic performance, a powder of the respective molecular sieves was pressed into tablets and the tablets were broken into pieces and sieved. TAME was reacted over the catalysts which were tested to determine their selectivity towards olefins, mainly ethylene and propylene from oxygenates. For the catalytic testing, the sieve fraction of 40-80 mesh was used. Prior to reaction, the molecular sieves were treated ex-situ in air at 550° C. for 2 hours.

The reaction was performed using a quartz reactor tube of 1.8 mm internal diameter. The molecular sieve samples were heated in nitrogen to the operating temperature and a mixture consisting of 6 vol % TAME balanced in $N_2$ was passed over the catalyst at atmospheric pressure (1 bar). The Gas Hourly Space Velocity (GHSV) is determined by the total gas flow over the zeolite weight per unit time (ml.gzeolite$^{-1}$.h$^{-1}$). The gas hourly space velocity used in the experiments was 10000 (ml.gzeolite$^{-1}$.h$^{-1}$). The effluent from the reactor was analyzed by gas chromatography (GC) to determine the product composition. The composition has been calculated on a weight basis of all hydrocarbons analyzed. The composition has been defined by the division of the mass of a specific product by the sum of the masses of all products. The effluent from the reactor obtained at several reactor temperatures was analyzed. The results are shown in Table 1.

For all tested catalyst, the conversion of TAME was complete. No TAME or methanol was detected in the effluent of the reactor.

The zeolite catalysts, i.e. ZSM-5, ZSM-22 and ZSM-23, show a good conversion of the TAME, including the isopentene part of the TAME, to ethylene and propylene. An advantage of the one-dimensional zeolites having 10-membered ring channels, i.e. ZSM-22 and ZSM-23, is the lower paraffin make and C6+ make compared to the multi-dimensional ZSM-5 zeolites.

By reducing the SAR of the ZSM-5 catalyst significantly less C4 olefins are produced.

The non-zeolite SAPO-34 catalyst shows high propylene to ethylene ratio compared to propylene to ethylene ratio reported in the art for conversion of methanol to ethylene and propylene over SAPO-34 catalyst. However, the SAPO-34 catalyst is less suitable for converting iso-C5 olefins as can be seen from the relative high C5 olefin content in the effluent of the reactor. These C5 olefins are preferably subsequently converted in an OCP reactor over a zeolite catalyst. It will be clear from table 1, that zeolite catalyst show a better conversion of C5 olefins to the desired ethylene and propylene products. Increasing the reaction temperature, results in a reduction of the C5 olefin content in the effluent of the reaction.

Example 2

Several molecular sieves were tested to show their ability to convert a mixture of TAME and methanol to an olefinic product. To test the molecular sieves for catalytic performance, a powder of the respective molecular sieves was pressed into tablets and the tablets were broken into pieces and sieved. A mixture of TAME and methanol was reacted over the catalysts which were tested to determine their selectivity towards olefins, mainly ethylene and propylene from oxygenates. For the catalytic testing, the sieve fraction of 40-80 mesh was used. Prior to reaction, the molecular sieves were treated ex-situ in air at 550° C. for 2 hours.

The reaction was performed using a quartz reactor tube of 1.8 mm internal diameter. The molecular sieve samples were heated in nitrogen to the operating temperature and a mixture consisting of 3 vol % TAME and 3 vol % methanol, balanced in $N_2$ was passed over the catalyst at atmospheric pressure (1 bar). The Gas Hourly Space Velocity (GHSV) is determined by the total gas flow over the zeolite weight per unit time (ml.gzeolite$^{-1}$.h$^{-1}$). The gas hourly space velocity used in the experiments was 10000 (ml.gzeolite$^{-1}$.h$^{-1}$). The effluent from the reactor was analyzed by gas chromatography (GC) to determine the product composition. The composition has been calculated on a weight basis of all hydrocarbons analyzed. The composition has been defined by the division of the mass of a specific product by the sum of the masses of all products.=The results are shown in Table 2.

From the results shown in Tables 1 and 2, it can be easily calculated that for the zeolite catalysts the ethylene and propylene yield in the effluent increases with the TAME concentration. As a result it can be concluded that blending TAME into a methanol feedstock to a zeolite catalyst-based OTO process will result in an improved yield of ethylene and propylene without requiring significant changes to the process operation. In case of a SAPO-34 catalyst the ethylene and propylene yield in the effluent reduces as TAME is added to the feed to the process, induced at least in part by the lesser ability of the SAPO-34 catalyst to convert the C5 iso-olefins. However, the addition of TAME to the feed of the OTO process does result in a higher ratio of propylene to ethylene in the effluent, which may be desirable in view of the relative

TABLE 1

| Temp [° C.] | | C2= [wt %] | C3= [wt %] | C4= [wt %] | C5 total [wt %] | C6 total (excl benzene) [wt %] | C7+ [wt %] | total aromatic [wt %] | Light ends [wt %] | C4 paraffin [wt %] |
|---|---|---|---|---|---|---|---|---|---|---|
| 525 | ZSM22 | 19.54 | 56.81 | 14.96 | 3.93 | 2.63 | 1.16 | 0.63 | 0.22 | 0.12 |
| 525 | ZSM23 | 20.34 | 54.93 | 15.94 | 3.39 | 2.75 | 1.52 | 0.63 | 0.31 | 0.19 |
| 525 | ZSM5 SAR280 | 20.08 | 45.16 | 18.59 | 4.15 | 2.62 | 2.61 | 4.98 | 1.37 | 0.45 |
| 525 | ZSM5 SAR80 | 26.58 | 39.13 | 12.78 | 6.13 | 1.70 | 2.73 | 7.94 | 0.28 | 2.72 |
| 420 | SAPO-34 | 7.50 | 15.23 | 17.97 | 52.74 | 4.34 | 1.38 | 0.37 | 0.16 | 0.32 |

TABLE 2

| Temp [° C.] | | C2= [wt %] | C3= [wt %] | C4= [wt %] | C5 total [wt %] | C6 total (excl benzene) [wt %] | C7+ [wt %] | total aromatic [wt %] | Light ends [wt %] | C4 paraffin [wt %] |
|---|---|---|---|---|---|---|---|---|---|---|
| 525 | ZSM22 | 14.80 | 54.52 | 20.40 | 4.29 | 2.61 | 1.77 | 0.95 | 0.47 | 0.19 |
| 525 | ZSM23 | 16.03 | 51.56 | 20.79 | 4.47 | 2.95 | 2.16 | 1.01 | 0.69 | 0.34 |
| 525 | ZSM5 SAR280 | 17.10 | 45.89 | 19.86 | 4.18 | 2.66 | 2.80 | 5.20 | 1.57 | 0.74 |
| 525 | ZSM5 SAR80 | 23.65 | 37.27 | 12.42 | 6.61 | 2.23 | 3.12 | 9.82 | 0.83 | 4.04 |
| 420 | SAPO-34 | 11.26 | 18.58 | 18.65 | 43.19 | 5.85 | 1.56 | 0.37 | 0.23 | 0.31 | low ratio of propylene to ethylene, typically around 1, generally observed for SAPO-34-based OTO processes described in the art.

Comparative Example A

The experiment of Example 1 was repeated for several zeolite catalyst. However, in this experiment TAME was replaced by MTBE.

In table 3, the ethylene and propylene yield and the ratio of propylene to ethylene in the effluent of the reactor are compared.

TABLE 3

|  | $C_2^=$ and $C_3^=$ yield | | ratio of $C_3^=$ to $C_2^=$ | |
| --- | --- | --- | --- | --- |
|  | Example 1 | Example A | Example 1 | Example A |
|  | [wt %] | | [—] | |
| ZSM22 | 0.77 | 0.57 | 2.9 | 2.3 |
| ZSM23 | 0.76 | 0.64 | 2.7 | 2.1 |
| ZSM5 SAR 280 | 0.66 | 0.58 | 2.2 | 2.2 |
| ZSM5 SAR 80 | 0.67 | 0.65 | 1.5 | 1.4 |

*SAR 80
SAR 280

As can be seen from Table 3, for all catalyst tested, the ethylene and propylene yield and the ratio of propylene to ethylene in the effluent of the reactor is increased when using TAME instead of MTBE.

What is claimed is:

1. A process for preparing ethylene and/or propylene and an iso-olefin-depleted olefinic product, comprising the steps of:
   a) providing a C5 hydrocarbon-comprising stream, comprising C5 cyclopentene and C5 iso-olefins;
   b) subjecting the C5 hydrocarbon-comprising stream to an etherification process with methanol and/or ethanol wherein at least part of the C5 iso-olefins are converted with methanol and/or ethanol to an tert-alkyl ether, and retrieving an etherification product stream;
   c) separating at least part of the etherification product stream into at least an ether-enriched stream and a first iso-olefin-depleted olefinic product;
   d) converting at least part of the tert-alkyl ether in the ether-enriched stream to ethylene and/or propylene by contacting at least part of the ether-enriched stream with a molecular sieve-comprising catalyst at a temperature in the range of from 350 to 1000° C. and retrieving a second olefinic product comprising ethylene and/or propylene.

2. A process according to claim 1, wherein the second olefinic product further comprises C5 olefins and wherein the process comprises the further steps:
   e) contacting at least part of the C5 olefins in the second olefinic product with a zeolite-comprising catalyst at a temperature in the range of from 350 to 1000° C. and converting at least part of the olefinic product into a further olefinic product comprising ethylene and/or propylene.

3. A process according to claim 2, wherein the zeolite-comprising catalyst comprises at least one zeolite selected from MFI, MEL, TON and MTT type zeolites.

4. A process according to claim 2, wherein the molecular sieve-comprising catalyst comprises at least one SAPO, AlPO, or MeAlPO type molecular sieve.

5. A process according to claim 3, wherein the molecular sieve-comprising catalyst comprises at least one SAPO, AlPO, or MeAlPO type molecular sieve.

6. A process according to claim 1, wherein in step (d) comprises contacting an oxygenate-comprising feedstock with the molecular sieve-catalyst and wherein the oxygenate-comprising feedstock comprises tert-alkyl ether obtained in step (b) and one or more other oxygenates, preferably at least one of one methanol and dimethylether.

7. A process according to claim 1, wherein the C5 iso-olefins are converted with methanol and/or ethanol to the tert-alkyl ether by contacting the C5 iso-olefin with methanol and/or ethanol in the presence of an etherification catalyst at a temperature in the range of from 30 to 100° C.

8. A process according to claim 7, wherein the etherification catalyst is a protonated cation-exchange resin catalyst.

9. A process according to claim 1, wherein in step (b) the C5 iso-olefins are converted with methanol to TAME.

10. A process according to claim 1, wherein the olefinic product comprises ethylene and at least part of the ethylene is further converted into at least one of polyethylene, monoethylene-glycol, ethylbenzene and styrene monomer.

11. A process according to claim 1, wherein the olefinic product comprises propylene and at least part of the propylene is further converted into at least one of polypropylene and propylene oxide.

12. A process according to claim 1, wherein at least part of the first iso-olefin-depleted olefinic product is used as blending components in the fuel pool.

13. A process according to claim 12, wherein the first iso-olefin-depleted olefinic product comprises methanol and/or ethanol.

14. A process according to claim 13, wherein in step (b) iso-olefins are converted with methanol to TAME and the first iso-olefin-depleted olefinic product comprises at least 8 wt % methanol.

15. A process according to claim 13, wherein in step (b) iso-olefins are converted with ethanol to TAEE and the first iso-olefin-depleted olefinic product comprises at least 4 wt % ethanol.

16. A process according to claim 14, wherein in step (b) iso-olefins are converted with ethanol to TAEE and the first iso-olefin-depleted olefinic product comprises at least 4 wt % ethanol.

* * * * *